United States Patent [19]

Glaeser et al.

[11] Patent Number: 4,897,504

[45] Date of Patent: * Jan. 30, 1990

[54] METHOD FOR AMMOXIDATION OF PARAFFINS AND CATALYST SYSTEM THEREFOR

[75] Inventors: Linda C. Glaeser, Lyndhurst; James F. Brazdil, Jr., Mayfield Village; Mark A. Toft, Lakewood, all of Ohio

[73] Assignee: The Standard Oil Company, Cleveland, Ohio

[*] Notice: The portion of the term of this patent subsequent to Nov. 28, 2006 has been disclaimed.

[21] Appl. No.: 270,188

[22] Filed: Nov. 14, 1988

Related U.S. Application Data

[60] Division of Ser. No. 204,475, Jun. 9, 1988, Pat. No. 4,837,191, which is a continuation-in-part of Ser. No. 194,665, May 16, 1988, Pat. No. 4,843,055.

[51] Int. Cl.$^4$ ............................................. C07C 120/14
[52] U.S. Cl. .................................................... 558/319
[58] Field of Search ........................................... 558/319

[56] References Cited

U.S. PATENT DOCUMENTS 4,760,159  7/1988  Suresh et al. ...................... 558/319

Primary Examiner—Joseph Paul Brust
Attorney, Agent, or Firm—C. S. Lynch; D. J. Untener; L. W. Evans

[57] ABSTRACT

Disclosed is ammoxidation of $C_3$ to $C_5$ acyclic alkanes with $NH_3$ and $O_2$ using (1) a mole ratio of alkane:$NH_3$ in the range from 2 to 16 and a mole ratio of alkane:$O_2$ in the range 1 to 10 and (2) a mixture of particulate catalyst compositions, the first being especially effective to promote formation of an unsaturated nitrile and an olefin from the paraffin, and the second catalyst composition being especially effective to promote the conversion of the olefin to the unsaturated mononitrile. Catalyst compositions useful in the process are also disclosed.

10 Claims, No Drawings

METHOD FOR AMMOXIDATION OF PARAFFINS AND CATALYST SYSTEM THEREFOR this is a division of application Ser. No. 204,475, filed June 9, 1988, now U.S. Pat. No. 4,837,191, which in turn is a continuation-in-part of application Ser. No. 194,665, filed May 16, 1988 now U.S. Pat. No. 4,843,055.

This invention relates to an improved process for the catalytic ammoxidation of paraffins containing from 3 to 5 carbon atoms to $\alpha,\beta$-unsaturated mononitriles, especially paraffins containing 3 to 4 carbon atoms. Most important is the ammoxidation of isobutane to methacrylonitrile and, especially, of propane to acrylonitrile.

Because of the price differential between propylene and propane an economic incentive exists for the development of a viable catalytic process for conversion of propane to acrylonitrile.

Earlier attempts in the prior art to develop an efficient process for the ammoxidation of propane to acrylonitrile produced either insufficient yields or processes that necessitated adding halogen promoters to the feed. The latter procedure would require not only reactors made of special corrosion resistant materials, but also the quantitative recovery of the promoter. The added costs thus eliminated the advantage of the propane/propylene price differential.

It is thus an object of the present invention to provide an improved process for the ammoxidation of paraffins to unsaturated mononitriles.

It is a further object of the invention to provide new catalyst systems for such process.

Still another object is to provide an improved catalytic ammoxidation process for making unsaturated mononitriles from lower paraffins without the use of halogen promoters.

Other objects, as well as aspects, features and advantages, of the present invention will become apparent from a study of the accompanying disclosure and the claims.

The foregoing and other objects of the present invention are achieved by the process of the present invention. There are two main features of the present process invention. The first of these is the use of an excess of the alkane feed with relation to $NH_3$ and molecular oxygen. The second feature, which is used in combination with the high ratio of the $C_3$ to $C_5$ paraffin to $NH_3$ and $O_2$, is that a combination, i.e., a mixture, of catalysts is employed, the first catalyst composition being especially effective to promote formation of an unsaturated mononitrile and an olefin from the paraffin, and the second catalyst composition being especially effective to promote the conversion of the olefin to the unsaturated nitrile. Such mixture is the subject of the composition claims herein.

In the present application "paraffin" designates an acyclic paraffin.

British Patent Specifications 1,336,135 and 1,336,136 disclose the use of high ratios of propane or isobutane to ammonia and oxygen, but only single ammoxidation catalysts are used, and the yields of acrylonitrile are extremely poor. U.S. Pat. No. 3,860,534 also discloses use of such high ratios, using a catalyst containing only V and Sb oxides. However, after the catalyst is calcined, it is washed for 24 hours with water and dried, a laborious procedure. A. N. Shatalova et al. in Neftekhiniya 8, No. 4, 609–612 (1968), describe the reaction of propane with oxygen and ammonia using a large excess of propane and a mixture of two catalysts, one of which is described as oxides of metals having dehydrogenating characteristics at 550° and 600° C. At 500° C. little or no acrylonitrile was produced. Rather large amounts of propionitrile and acrolein were made per mole of acrylonitrile produced. The per pass conversion of propane to acrylonitrile was generally 2–4 percent with selectivity to acrylonitrile being from 12 to 33 percent.

In the present process when applied to propane ammoxidation a small amount of propylene is produced in relation to the unreacted propane in the effluent. Such propane effluent containing propylene in the amount of up to 8 mole percent, but usually no more than 6 mole percent, of the amount of propane plus propylene can comprise the substrate feed to the present process. And in general the $C_3$ to $C_5$ alkene feed to the process can contain one or more $C_3$ to $C_5$ olefins. The $C_3$ to $C_5$ olefin content of the feed to the present ammoxidation process can contain from zero to 8 mole percent of such olefin(s), based on the moles of $C_3$ to $C_5$ paraffin plus olefins fed, and this feed can be from any source. Although larger amounts of $C_3$ to $C_5$ olefins may be present in the substrate paraffin feed, usual amounts are as stated, and the usual olefin is that corresponding to the particular paraffin fed to the reaction zone of the present process.

According to one aspect of the present invention there is provided a process for the ammoxidation of a $C_3$ to $C_5$ paraffin to an $\alpha,\beta$-unsaturated mononitrile which comprises contacting in a reaction zone said paraffin in the vapor phase in admixture with ammonia, molecular oxygen, and optionally an inert gaseous diluent, with an intimate particulate mixture of a first catalyst composition and a second catalyst composition, said feed to the reaction zone containing a mole ratio of paraffin:$NH_3$ in the range from 2 to 16 (usually 3–7), and a mole ratio of paraffin to $O_2$ in the range from 1 to 10 (usually 1.5–5), said first catalyst composition being 0–99 weight percent of a diluent/support and 100–1 weight percent of a catalyst having oxygen and the cation components in the proportions indicated by the empirical formula:

$$Bi_aV_bL_lM_mT_tO_x, \qquad \text{formula (1)}$$

wherein
L is one or more of K, Cs, Rb and Tl;
M is one or more of Mo, W, Cr, Ge, Sb, Sn, P, Pb and B;
T is one or more of Zn, Nb, Ta, Fe, Co, Ni Cu, Mn, Ti and rare earths;
a=1–25
b=1–50
l=0–1, usually 0–0.2
m=0.1–20
t=0–20
x is determined by the oxidation state of the other elements in the catalyst,
(a+b):(l+m+t)=20:1 to 1:5
a:b=1:5–5:1, usually 1:3–3:1,
with the proviso that the atomic ratio of Mo:V is zero to <10; said second catalyst composition being 0–99 weight percent of a diluent/support and 100–1 weight percent of a catalyst having oxygen and the cation components in the proportions indicated by the empirical formula:

$$Bi_kFe_jMo_{12}V_yD_dE_eF_fG_gO_x \qquad \text{formula (2)}$$

where
- D is one or more of an alkali metal, Sm, Ag
- E is one or more of Mn, Cr, Cu, Zn, Cd, La,
- F is one or more of P, As, Sb, Te, W, B, Sn, Pb, Se
- G is one or more of Co, Ni, alkaline earth metal and
- k is 0.1–12, l is 0.01–12, v is 0–0.5, d is 0–0.5, e is 0–10, f is 0–10, g is 0–12, $v+k+l+d+e+f+g \leqq 24$, and x is a number determined by the valence requirements of the other elements present, wherein the weight ratio in said mixture of said first catalyst composition to said second catalyst composition is in the range of 0.001 to 2.5.

By "particulate mixture" as used herein is meant a mixture of solid particles or subdivided pieces of the first catalyst composition with separate and distinct solid particles of the second catalyst composition. The particles are often of a size used in fluidized bed reactors, say about 40 to 90 microns, but of course larger particles of catalyst can be employed for use in fixed or gravity flowing catalyst beds.

"Rare earths" as used herein means atomic numbers 57 through 71.

In the present process in all its embodiments the ratio of $O_2$ to $NH_3$ fed to the reaction zone is usually in the range from 1 to 10 (more often 1–5) and the ratio of inert gaseous diluent to paraffin is usually in the range zero to 5 (more often zero to 3).

The diluent or support for either catalyst composition is a refractory metal oxide or mixture, such as silica, silica-alumina, etc.

In the usual practice of the present invention the catalyst support/diluent for the catalyst of formula (1) is not an oxide of an element named in formula (1). Further, in the usual practice of the invention the catalyst support/diluent for the catalyst of formula (2) is not an oxide of an element named in formula (2).

In the catalyst compositions of the invention the catalyst empirical formulas (1) and (2) do not, of course, connote any particular chemical compound, nor indicate whether the elements are present as a mixture of individual oxides or as a complex oxide or oxides, or what separate crystalline phases or solid solutions may be present. Similarly, the designation of certain oxides, such as "silica" or "alumina" or $SiO_2$ or $Al_2O_3$, as supports or diluents is merely in accordance with convention in the inorganic oxide catalyst art, and such designations refer to compounds often regarded as supports in the catalyst art. Such designations, however, do not mean that the element involved is actually present as a simple oxide. Indeed, such elements may at times be present as a complex oxide with one, more than one, or all of the elements in formula (1) or formula (2), which complex oxides form during the precipitation or agglomeration, drying and calcining process for preparing the catalyst composition.

The process of the invention is especially useful in the ammoxidation of propane or isobutane.

In the preparation of the catalyst compositions of formula (1) or formula (2) the metal oxides can be blended together or can be formed separately and then blended or formed separately or together in situ. Promoter oxides are conveniently incorporated into the bismuth-iron-molybdenum based catalyst by blending into the gel before calcining or by blending into the oven-dried base catalyst before calcining. A useful manner of incorporating promoter elements is by choosing a water-soluble salt of the promoter element, forming an aqueous solution of the salt, and mixing the solution with a solution or a suspension of the base elements or salts thereof. Optionally, the promoter elements may be incorporated by the use of soluble complex salts or compounds with the desired base elements which upon calcination will yield the desired ratio of the elements in the finished catalyst.

Bismuth may be introduced into the catalyst as an oxide or as any salt which upon calcination will yield the oxide. Most preferred are the water-soluble salts which are easily dispersible within the catalyst and which form stable oxides upon heat-treating. The most preferred salt for introducing bismuth is bismuth nitrate.

To introduce the iron component into the catalysts one may use any compound of iron which, upon calcination, will result in the oxides. As with the other elements, water soluble salts are preferred for the ease with which they may be uniformly dispersed within the catalyst. Most preferred is ferric nitrate. Cobalt and nickel are similarly introduced.

To introduce the molybdenum component any molybdenum oxide such as the dioxide, trioxide, pentoxide or sesquioxide may be used; more preferred is hydrolyzable or decomposable molybdenum salt such as molybdenum halide. A preferred starting material is ammonium heptamolybdate.

Other variations in starting materials will suggest themselves to one skilled in the art, particularly when the preferred starting materials mentioned hereinabove are unsuited to the economics of large-scale manufacture. In general, any compounds containing the desired catalyst components may be used provided that they result, upon heating to a temperature within the range disclosed hereinafter, in the oxides of the instant catalyst.

These catalyst compositions can conveniently be prepared by slurry techniques wherein an aqueous slurry containing all of the elements in the objective catalyst is produced. In any event, a solution or slurry containing all of the elements of the catalyst is formed. This is followed by evaporation, drying and then calcining the product in a molecular oxygen-containing atmosphere, such as air, at from 350° to 700° or 750° C., usually 400° to 650° C. The length of the calcination period may range from 30 minutes to 12 hours, but satisfactory catalyst compositions are usually obtained by calcination at such temperatures for a period of from 1 to 5 hours. Until calcination the compositions are not catalysts but are merely precatalysts with little or no catalytic activity. Liquids other than water, such as $C_1$ to $C_8$ alcohols can also be used to form the precatalyst slurry.

In the ammoxidation of the present invention, the reaction is carried out in the gas phase by contacting a mixture of the paraffin, ammonia and molecular oxygen, and inert diluent, if any, conveniently in a fixed bed of the catalyst mixture, or a gravity flowing bed, a fluidized bed or a fast transport reactor mode.

Examples of inert diluents useful in the reaction are $N_2$, He, $CO_2$, $H_2O$ and Ar.

The reaction temperature range can vary from 350° to 700° C., but is usually 430° to 520° C. The latter temperature range is especially useful in the case of propane ammoxidation to acrylonitrile.

The average contact time can often be from 0.01 to 10 seconds, but is usually from 0.02 to 10 seconds, more usually from 0.1 to 5 seconds.

The pressure of the reaction usually ranges from 2 to 45 psia. Most often, pressure is somewhat above atmospheric.

The following examples of the invention are exemplary and should not be taken as in any way limiting.

EXAMPLE 1

A solution containing chromium nitrate and bismuth nitrate dissolved in dilute nitric acid was mixed with a solution containing ammonium metavanadate and ammonium heptamolybdate dissolved in hot water. Silica sol and alumina sol were added to this and the slurry was evaporated to dryness over a hot plate. The dry material was heat treated at 290° C./3 hours, 425° C./3 hours, and 610° C./3 hours. The composition of the catalyst was 50% $BiV_{0.7}Mo_{0.5}CrO_x + 25\%$ $SiO_2 + 2-5\% Al_2O_3$.

EXAMPLE 2

Ammonium heptamolybdate was dissolved in water. Silica sol was added, followed by $CrO_3$. Iron nitrate was melted on a hotplate with a small amount of water. Then, in order, were added manganese, bismuth, cobalt and nickel nitrates, forming a solution that was added to the Mo—Cr—Si solution previously prepared, forming a slurry which was heated on a hotplate with stirring until it started to thicken. It was then dried at 120° C., heated 3 hours at 290° C. and 3 hours at 425° C.

The composition was then ground to 20-35 mesh and heated for 3 hours at 610° C. The catalyst composition was 50% $Ni_{2.5}Co_{4.5}Fe_2MnBiCr_{0.5}Mo_{13.2}O_x + 50\%$ $SiO_2$

EXAMPLE 3

A catalyst having the empirical composition 50% $Ni_{2.5}Co_{4.5}Fe_2MnBiCr_{0.5}Mo_{10}O_x + 50\%$ $SiO_2$ was made in the manner of Example 2.

EXAMPLE 4

Ammonium heptamolybdate was dissolved in water. Silica sol was added, followed by $CrO_3$. Iron nitrate was melted on a hotplate with a small amount of water. Then, in order, were added manganese, bismuth, magnesium and nickel nitrates, forming a solution that was added to the Mo—Cr—Si solution previously prepared, forming a slurry which was heated on a hotplate with stirring until it started to thicken. It was then dried at 120° C., heated 3 hours at 290° C. and 3 hours at 425° C.

The composition was then ground to 20-35 mesh and heated for 3 hours at 610° C. the catalyst composition was 50% $Mg_2Ni_5Fe_2MnBiCr_{0.5}Mo_{13.2}O_x + 50\%$ $SiO_2$.

EXAMPLE 5

69.92 g of $(NH_4)_6Mo_7O_{24}.4H_2O$ were dissolved in 200 cc of warm water. 222.27 g of a 40 wt% silica sol was added, then 3.0 g of $CrO_3$, forming an orange solution. Then 24.24 g of $Fe(NO_3)_3.9H_2O$ were melted on a hotplate with a small amount of water. Then, in order listed, 10.74 g of $Mn(NO_3)_2$ (a 50 wt% solution in water), 14.55 g $Bi(NO_3)_3.5H_2O$, 39.29 g $Co(NO_3)_2.6H_2O$ and 21.81 g $Ni(NO_3)_2.6H_2O$ were added, forming a dark brown solution. The latter solution was added to the orange solution, forming a pale yellow slurry, which was heated on a hotplate with constant stirring until it started to thicken; it was then dried at 120° C., then heated at 290° C. for 3 hours and 425° C. for 3 hours, then ground to about 20-35 mesh size. A portion of the catalyst was then calcined by heating at 610° C. for 3 hours. The catalyst composition was 50 wt% $Ni_{2.5}Co_{4.5}Fe_2MnBiCrMo_{13.2}O_x + 50$ wt% $SiO_2$.

EXAMPLE 6

Ammonium heptamolybdate was dissolved in water. The ammonium metatungstate was added, followed by silica sol and then $CrO_3$. Iron nitrate was melted on a hotplate with a small amount of water. Then, in order, were added manganese, bismuth, cobalt and nickel nitrates, forming a solution that was added to the Mo—Cr—Si solution previously prepared, forming a slurry which was heated on a hotplate with stirring until it started to thicken. It was then dried at 120° C., heated 3 hours at 290° C. and 3 hours at 425° C.

The composition was then ground to 20-35 mesh and heating for 3 hours at 610° C. The catalyst composition was 50% $Co_{4.5}Ni_{2.5}Fe_2BiMnCr_{0.5}Mo_{12}W_{1.2}O_x + 50\%$ $SiO_2$.

EXAMPLE 7

69.92 g of $(NH_4)_6Mo_7O_{24}.4H_2O$ were dissolved in 200 cc of warm water and 216.57 g of a 40 wt% silica sol was added, forming a first solution. Then 24.24 g of $Fe(NO_3)_3.9H_2O$ were melted on a hotplate with a small amount of water. Then, in order listed, 10.74 g of $Mn(NO_3)_2$ (a 50 wt% solution in water), 14.55 g $Bi(NO_3)_3.5H_2O$, 39.29 g $Co(NO_3)_2.6H_2O$ and 21.81 g $Ni(NO_3)_2.6H_2O$ were added, forming a dark brown solution. The latter solution was added to the first solution, forming a slurry, which was heated on a hotplate with constant stirring until it started to thicken; it was then dried at 120° C., then heated at 290° C. for 3 hours and 425° C. for 3 hours, then ground to about 20-35 mesh size. A portion of the catalyst was then calcined by heating at 610° C. for 3 hours. The catalyst compositions was 50 wt% $Co_{4.5}Ni_{2.5}Fe_2MnBiMo_{13.2}O_x + 50\%$ $SiO_2$ support.

EXAMPLE 8

Ammonium heptamolybdate was dissolved in water. Silica sol was added, followed by $CrO_3$. Iron nitrate was melted on a hotplate with a small amount of water. Then, in order, were added manganese, bismuth, cobalt and nickel nitrates, forming a solution that was added to the Mo—Cr—Si solution previously prepared, forming a slurry which was heating on a hotplate with stirring until it started to thicken. It was then dried at 120° C., heated 3 hours at 290° C. and 3 hours at 425° C.

The composition was then ground to 20-35 mesh and heated for 3 hours at 610° C. The catalyst composition was 50% $Ni_{2.5}Co_{4.5}Fe_2MnBiCr_{0.5}Mo_{12}O_x + 50\%$ $SiO_2$.

EXAMPLE 9

Ammonium heptamolybdate was dissolved in water. The ammonium metatungstate was added, followed by silica sol and then $CrO_3$. Iron nitrate was melted on a hotplate with a small amount of water. Then, in order, were added manganese, bismuth, cobalt and nickel nitrates, forming a solution that was added to the Mo—Cr—Si solution previously prepared, forming a slurry which was heated on a hotplate with stirring until it started to thicken. It was then dried at 120° C., heated 3 hours at 290° C. and 3 hours at 425° C. The composition was then ground to 20-35 mesh and heated for 3 hours at 610° C. The catalyst composition was 50% $Co_{4.5}Ni_{2.5}Fe_2BiMnCr_{0.5}Mo_{10}W_2O_x + 50\%$ $SiO_2$.

EXAMPLE 10

Ammonium heptamolybdate was dissolved in water. Silica sol was added, followed by $CrO_3$. Iron nitrate was melted on a hotplate with a small amount of water. Then, in order, were added manganese, bismuth, cobalt, nickel and potassium nitrates, forming a solution that was added to the Mo—Cr—Si solution previously prepared, forming a slurry which was heated on a hotplate with stirring until it started to thicken. It was then dried at 120° C., heated 3 hours at 290° C. and 3 hours at 425° C.

The composition was then ground to 20-35 mesh and heated for 3 hours at 610° C. The catalyst composition was 50% $K_{0.05}Ni_{2.5}Co_{4.5}Fe_2MnBiCr_{0.5}Mo_{12}O_x$ + 50% $SiO_2$.

EXAMPLE 11

Ammonium heptamolybdate was dissolved in water. Silica sol was added, followed by $CrO_3$. Iron nitrate was melted on a hotplate with a small amount of water. Then, in order, were added manganese, bismuth, cobalt, nickel and potassium nitrates, forming a solution that was added to the Mo—Cr—Si solution previously prepared, forming a slurry which was heated on a hotplate with stirring until it started to thicken. It was then dried at 120° C., heated 3 hours at 290° C. and 3 hours at 425° C.

The composition was then ground to 20-35 mesh and heated for 3 hours at 610° C. The catalyst composition was 50% $K_{0.05}Ni_{2.5}Co_{4.5}Fe_2MnBiCr_{0.5}Mo_{13.2}O_x$ + 50% $SiO_2$.

EXAMPLE 12

A catalyst having the composition 50% $Fe_{6.6}Bi_{4.2}P_{1.2}Mo_{12}O_x$ + 50% $SiO_2$ was made as follows: 63.56 g of ammonium heptamolybdate was dissolved in 200 ml of water. 4.15 g of 85% $H_3PO_4$ was added to this solution and then 248.85 g of a 40 wt.% silica sol.

In a separate beaker 80 g of ferric nitrate was wetted with about 15 ml of water at about 60° C. Then 61.12 g of bismuth nitrate was dissolved in this solution. The resulting solution was added slowly with stirring to the other mixture, and the resulting slurry was heated with stirring to remove excess water. When it no longer could be stirred it was dried overnight at about 120° C., heated 3 hours at 290° C. and then 3 hours at 425° C. It was ground and screened to 20-35 mesh and a portion calcined at 610° C. for 3 hours.

EXAMPLE 13

A catalyst having the composition 50% $K_{0.05}Fe_{6.6}Bi_{4.2}P_{1.2}Mo_{12}O_x$ + 50% $SiO_2$ was made as follows: 63.56 g of ammonium heptamolybdate was dissolved in 200 ml of water 4.15 g of 85% $H_3PO_4$ was added to this solution and then 249.02 g of a 40 wt. % silica sol.

In a separate beaker 80 g of ferric nitrate was wetted with about 15 ml of water at about 60° C. Then 61.12 g of bismuth nitrate was dissolved in this solution, followed by 1.52 g of a 10 wt% solution of $KNO_3$. The resulting solution was added slowly with stirring to the other mixture, and the resulting slurry was heated with stirring to remove excess water. When it no longer could be stirred it was dried overnight at about 120° C., heated 3 hours at 290° C. and then 3 hours at 425° C. It was ground and screened to 20-35 mesh and a portion calcined at 610° C. for 3 hours.

EXAMPLE 14

A catalyst having the composition 50% $Fe_{6.6}Bi_{4.2}P_{1.2}Mo_{10}O_x$ + 50% $SiO_2$ was made as follows: 52.97 g of ammonium heptamolybdate was dissolved in 200 ml of water. 4.15 g of 85% $H_3PO_4$ was added to this solution and then 227.26 g of a 40 wt. % silica sol.

In a separate beaker 80 g of ferric nitrate was wetted with 15 ml of water at about 60° C. Then 61.12 g of bismuth nitrate was dissolved in this solution. The resulting solution was added slowly with stirring to the other mixture, and the resulting slurry was heated with stirring to remove excess water. When it no longer could be stirred it was dried overnight at about 120° C., heated 3 hours at 290° C. and then 3 hours at 425° C. It was ground and screened to 20-35 mesh and a portion calcined at 610° C. for 3 hours.

EXAMPLE 15

A catalyst having the composition 50% $Fe_{6.6}Bi_{4.2}P_{1.2}Mo_8O_x$ + 50% $SiO_2$ was made in the same manner as Example 14.

EXAMPLE 16

A catalyst having the composition 50% $Fe_{6.6}Bi_{4.2}P_{1.2}Mo_{10}W_2O_x$ + 50% $SiO_2$ was made as follows: 52.97 g of ammonium heptamolybdate was dissolved in 200 ml of water. 16.37 g of ammonium metatungstate (85% $WO_3$) was then added, followed by 4.15 g of 85% $H_3PO_4$ and then 262.03 g of a 40 wt. % silica sol.

In a separate beaker 80 g of ferric nitrate was wetted with about 15 ml of water at about 60° C. Then 61.12 g of bismuth nitrate was dissolved in this solution. The resulting solution was added slowly with stirring to the other mixture, and the resulting slurry was heating with stirring to remove excess water. When it no longer could be stirred it was dried overnight at about 120° C., heated 3 hours at 290° C. and then 3 hours at 425° C. It was ground and screened to 20-35 mesh and a portion calcined at 610° C. for 3 hours.

EXAMPLE 17

Ammonium heptamolybdate was dissolved in water. Silica sol was added, followed by $CrO_3$. The silica was 70% silica sol and 30% Aerosil 200. Iron nitrate was melted on a hotplate with a small amount of water. Then, in order, were added manganese, bismuth, cobalt and nickel nitrates, forming a solution that was added to the Mo—Cr—Si solution previously prepared, forming a slurry which was heated on a hotplate with stirring until it started to thicken. It was then dried at 120° C., heated 3 hours at 290° C. and 3 hours at 425° C.

The composition was then ground to 20-35 mesh and heated for 3 hours at 610° C. The catalyst composition was 50% $Ni_{2.5}Co_{4.5}Fe_2MnBiCr_{0.5}Mo_{13.2}O_x$ + 50% $SiO_2$.

EXAMPLE 18

A catalyst having the composition, 50% $BiVO_x$ + 25% $SiO_2$ + 25% $Al_2O_3$, was made as follows:

37.4 g of bismuth nitrate dissolved in dilute nitric acid (10%) was added to 9.0 g of ammonium metavanadate dissolved in hot water. 31.2 g of silica sol and 62.5 g alumina sol were added to this, and the resultant slurry was then worked up as in Example 17.

EXAMPLE 19

Bismuth nitrate dissolved in dilute nitric acid was mixed with a solution containing ammonium metavanadate and ammonium heptamolybdate dissolved in hot water. Silica sol and alumina sol were added to this and the slurry was evaporated to near dryness over a hot plate. The dry material was heat treated at 290° C./3 hours, 425° C./3 hours, ground and screened to 20–35 mesh and heated at 610° C./3 hours. The composition of the catalyst was 50% $BiV_{0.7}MoO_x$+25% $SiO_2$+25% $Al_2O_3$.

COMPOSITION OF CATALYST MIXTURES

Mixture A

This is a mixture of the catalysts of Example 6 and Example 1 with a weight ratio of the latter to the former of 0.15.

Mixture B

This is a mixture of the catalysts of Example 4 and Example 1 with a weight ratio of the latter of the former of 0.15.

Mixture C

This is a mixture of the catalysts of Example 7 and Example 1 with a weight ratio of the latter of the former of 0.15.

Mixture D

This is a mixture of the catalysts of Example 8 and Example 1 with a weight ratio of the latter to the former of 0.15.

Mixture E

This is a mixture of the catalysts of Example 9 and Example 1 with a weight ratio of the latter to the former of 0.15.

Mixture F

This is a mnixture of the catalysts of Example 5 and Example 1 with a weight ratio of the latter to the former of 0.15.

Mixture G

This is a mixture of the catalysts of Example 14 and Example 1 with a weight ratio of the latter to the former of 0.15.

Mixture H

This is a mixture of the catalysts of Example 15 and Example 1 with a weight ratio of the latter to the former of 0.15.

Mixture I

This is a mixture of the catalysts of Example 3 and Example 1 with a weight ratio of the latter to the former of 0.15.

Mixture J

This is a mixture of the catalysts of Example 13 and Example 1 with a weight ratio of the latter to the former of 0.15.

Mixture K

This is a mixture of the catalysts of Example 10 and Example 1 with a weight ratio of the latter to the former of 0.15.

Mixture L

This is a mixture of the catalysts of Example 12 and Example 1 with a weight ratio of the latter to the former of 0.15.

Mixture M

This is a mixture of the catalysts of Example 16 and Example 1 with a weight ratio of the latter to the former of 0.15.

Mixture N

This is a mixture of the catalysts of Example 11 and Example 1 with a weight ratio of the latter of the former of 0.15.

Mixture O

This is a mixture of the catalysts of Example 2 and Example 1 with a weight ratio of the latter to the former of 0.15.

Mixture P

This is a mixture of the catalysts of Example 17 and Example 1 with a weight ratio of the latter to the former of 0.15.

Mixture Q

This is a mixture of the catalysts of Example 4 and Example 18 with a weight ratio of the latter to the former of 0.15.

Mixture R

This is a mixture of the catalysts of Example 4 and Example 19 with a weight ratio of the latter to the former of 0.15.

In the ammoxidation runs of the following examples summarized in Table 1, the mixture of catalysts is in a tubular ⅜ inch I.D. stainless steel fixed bed reactor. To make the mixture of particulate catalysts, the desired weight of each of the two catalyst compositions is put in a vial and shaken until uniformly dispersed before placing the desired amount of the catalyst mixture in the reaction tube. The reactor is equipped with a preheat leg and is immersed in a temperature controlled molten salt bath. The gaseous feed components are metered through mass flow controllers into the bottom of the reactor through the preheat leg. Water is introduced through a septum at the top of the preheat leg, using a syringe pump. The feed is fed to the catalyst for a pre-run of 1 hour before collection of product unless a longer pre-run time is noted; the runs of each example last 30–60 minutes during which the product is collected for analysis. In the ammoxidation runs shown in Table 1 the molar ratios of propane:$NH_3$:$O_2$:$H_2O$ were 5/1/2/1.

In Table 1, Example 36 is a comparative run and is not an example of the invention. Nor is catalyst mixture Q.

TABLE 1

| Example | Catalyst Mixture | Temp, °C. | CT Secs (4) | Percent Propane Conversion | Propane: Mole % Conversion to | | | | | % Selectivity Based on Propane | | |
|---|---|---|---|---|---|---|---|---|---|---|---|---|
| | | | | | (2) AN | HCN | AN + HCN | (3) $C_3=$ | AN + $C_3=$ | AN | AN + HCN | AN + $C_3=$ |
| 20(5) | A | 470 | 1.7 | 11.8 | 6.7 | 1.0 | 7.7 | 0.9 | 7.5 | 56.6 | 65.3 | 63.9 |
| 21(5) | B | 470 | 1.5 | 12.3 | 7.5 | 0.7 | 8.2 | 0.8 | 7.3 | 61.0 | 66.6 | 67.3 |
| 22(6) | C | 470 | 2.2 | 12.6 | 6.8 | 0.7 | 7.5 | 1.2 | 7.9 | 53.6 | 58.8 | 62.8 |
| 23 | D | 470 | 1.5 | 11.5 | 6.3 | 0.4 | 6.7 | 1.0 | 7.3 | 54.7 | 58.2 | 63.9 |
| 24(7) | E | 470 | 1.6 | 11.4 | 6.2 | 0.6 | 6.8 | 1.0 | 7.1 | 54.4 | 59.3 | 62.9 |
| 25(6) | F | 470 | 1.4 | 10.7 | 5.9 | 0.7 | 6.6 | 1.6 | 7.5 | 55.6 | 62.3 | 70.4 |
| 26(1)(8) | G | 470 | 1.6 | 12.4 | 6.6 | 1.3 | 7.9 | 0.6 | 7.2 | 53.1 | 63.7 | 58.1 |
| 27(1)(7) | H | 470 | 1.6 | 10.8 | 5.3 | 0.9 | 6.2 | 0.6 | 5.9 | 49.1 | 57.9 | 55.2 |
| 28 | I | 470 | 1.6 | 11.6 | 6.5 | 0.6 | 7.1 | 1.0 | 7.5 | 55.5 | 60.4 | 64.0 |
| 29(1)(8) | J | 470 | 1.5 | 10.0 | 4.9 | 0.7 | 5.6 | 0.8 | 5.7 | 49.2 | 56.1 | 56.9 |
| 30(7) | K | 470 | 1.5 | 12.9 | 6.5 | 0.7 | 7.2 | 0.9 | 7.4 | 50.5 | 56.0 | 57.6 |
| 31(1)(9) | L | 470 | 1.5 | 10.3 | 5.4 | 0.7 | 6.1 | 0.6 | 6.0 | 52.3 | 58.9 | 58.6 |
| 32(1)(9) | M | 470 | 1.6 | 11.0 | 5.5 | 1.2 | 6.7 | 1.0 | 6.5 | 49.5 | 60.3 | 58.3 |
| 33(5) | N | 470 | 1.5 | 10.7 | 6.2 | 0.6 | 6.8 | 1.0 | 7.2 | 57.5 | 63.5 | 66.5 |
| 34(6) | O | 470 | 1.4 | 11.3 | 6.4 | 0.5 | 6.9 | 0.8 | 7.2 | 56.7 | 61.2 | 64.1 |
| 35(7) | P | 470 | 1.7 | 11.7 | 6.4 | 0.5 | 6.9 | 1.1 | 7.5 | 54.5 | 58.8 | 63.8 |
| 36 | Q | 470 | 1.6 | 8.2 | 3.0 | 0.3 | 3.3 | 0.6 | 3.6 | 36.2 | 40.1 | 42.9 |
| 37 | R | 470 | 1.6 | 6.7 | 3.9 | 0.3 | 4.2 | 0.5 | 4.4 | 59.1 | 64.2 | 66.3 |

(1) Catalyst Mixture was reduced for 15 min. at 470° C. with NH3 before pre-run.
(2) AN is Acrylonitrile
(3) $C_3=$ is Propylene
(4) Contact, Time, Seconds
(5) The feed was fed to the reactor for 72 hrs before collecting product for analysis.
(6) The feed was fed to the reactor for 48 hrs before collecting product for analysis.
(7) The feed was fed to the reactor for 24 hrs before collecting product for analysis.
(8) The feed was fed to the reactor for 96 hrs before collecting product for analysis.
(9) The feed was fed to the reactor for 216 hrs before collecting product for analysis.

As will be evident to those skilled in the art various modifications of this invention can be made or followed in the light of the foregoing disclosure and discussion without departing from the spirit and scope of the disclosure or from the scope of the claims.

We claim:

1. A process for the ammoxidation of a $C_3$ to $C_5$ paraffin to an $\alpha,\beta$-unsaturated mononitrile which comprises contacting in a reaction zone said paraffin in the vapor phase in admixture with ammonia, molecular oxygen, and optionally an inert gaseous diluent, with an intimate particulate mixture of a first catalyst composition and a second catalyst composition, said feed to the reaction zone containing a mole ratio of paraffin:$NH_3$ in the range of 2 to 16, and a mole ratio of parrafin:$O_2$ in the range from 1 to 10 said first catalyst composition being 0-99 weight percent of a diluent/support and 100-1 weight percent of a catalyst having oxygen and the cation components in the proportions indicated by the empirical formula:

$$Bi_aV_bL_lM_mT_tO_x,\qquad \text{formula (1)}$$

wherein

L is one or more of K, Cs, Rb and Tl;

M is one or more of Mo, W, Cr, Ge, Sb, Sn, P, Pb and B;

T is one or more of Zn, Nb, Ta, Fe, Co, Ni Cu, Mn, Ti and rare earths, a=1-25
b=1-50
l=0-1
m=0.1-20
t=0-20 x is determined by the oxidation state of the other elements in the catalyst, (a+b):(l+m+t)=20:1 to 1:5
a:b=1:5-5:1 with the proviso that the atomic ratio of Mo:V is zero to <10; said second catalyst composition being 0-99 weight percent of a diluent/support and 100-1 weight percent of a catalyst having oxygen and the cation components in the proportions indicated by the empirical formula:

$$Bi_kFe_fMo_{12}V_vD_dE_eF_fG_gO_x \qquad \text{formula (2)}$$

where

D is one or more of an alkali metal, Sm, Ag

E is one or more of Mn, Cr, Cu, Zn, Cd, La,

F is one or more of P, As, Sb, Te, W, B, Sn, Pb, Se

G is one or more of Co, Ni, alkaline earth metal, and k is 0.1-12, l is 0.01-12, v is 0-0.5, d is 0-0.5, e is 0-10, f is 0-10, g is 0-12, v+k+l+d+e+f+g≦24, and x is a number determined by the valence requirements of the other elements present, wherein the weight ratio in said mixture of said first catalyst composition to said second catalyst composition is in the range of 0.001 to 2.5.

2. A process of claim 1 wherein said mole ratio of paraffin:$NH_3$ is in the range from 3 to 7.

3. A process of claim 1 wherein said mole ratio of paraffins:$O_2$ is in the range from 1.5 to 5.

4. A process of claim 2 wherein said mole ratio of paraffin:$O_2$ is in the range from 1.5 to 5.

5. A process according to claim 1 wherein the mole ratio of $O_2$ to $NH_3$ in the feed to the reaction zone is in the range from 1 to 10.

6. A process according to claim 1 wherein the mole ratio of inert gaseous diluent to paraffin in the feed to the reaction zone is in the range from zero to 5.

7. A process of claim 1 wherein said paraffin is propane or isobutane.

8. A process of any one of any one of claim 1 wherein said paraffin is propane.

9. A process of claim 2 wherein said paraffin is propane or isobutane.

10. A process of claim 4 wherein said paraffin is propane.

* * * * *